Figure 1:
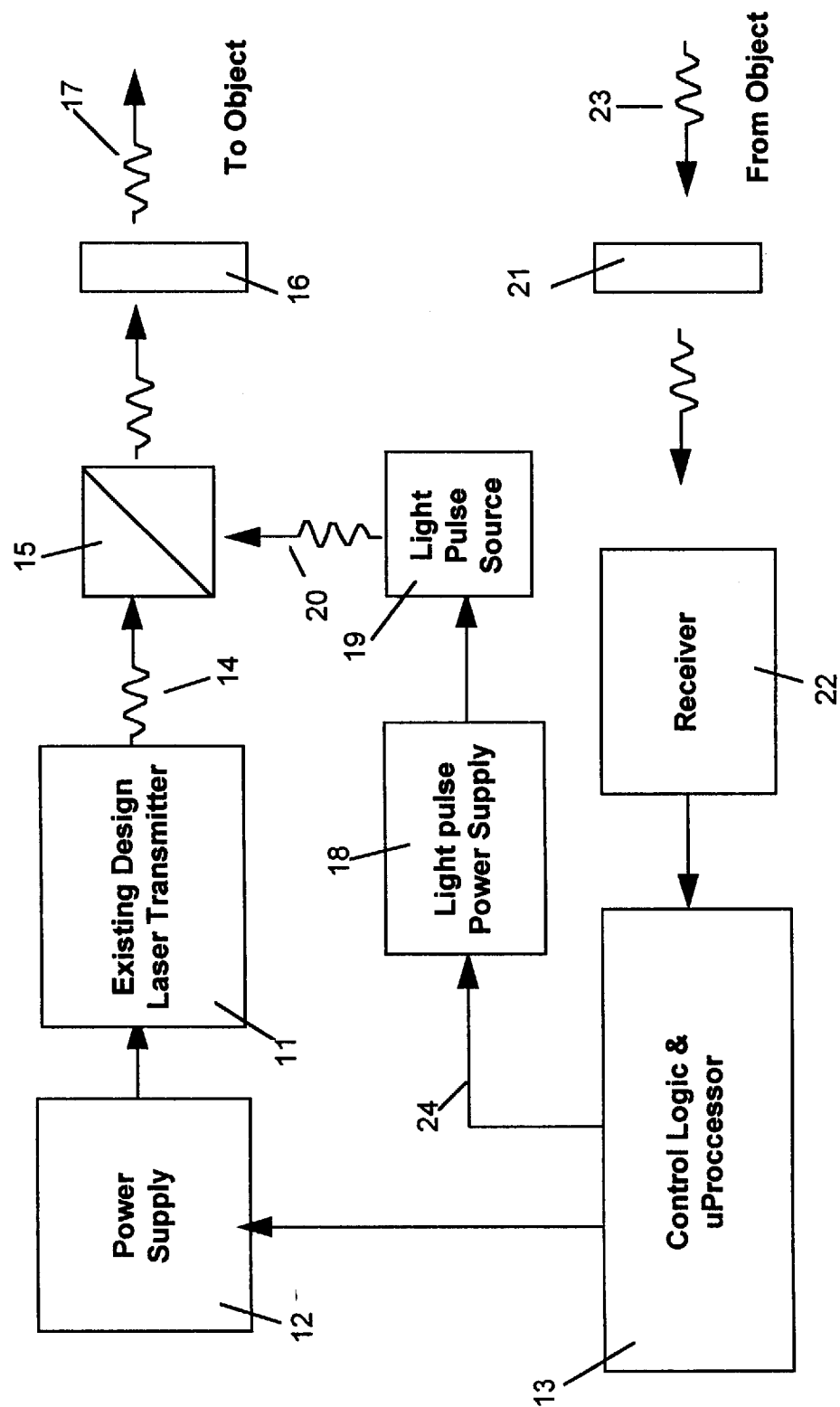

United States Patent

Keydar

[11] Patent Number: 5,837,996
[45] Date of Patent: Nov. 17, 1998

[54] EYE PROTECTION SYSTEM WHEREIN A LOW POWER LASER CONTROLS A HIGH POWER LASER

[76] Inventor: Eytan Keydar, 4 Hatekuma Street, Rehovot 76217, Israel

[21] Appl. No.: 887,146

[22] Filed: Jul. 2, 1997

Related U.S. Application Data

[63] Continuation of Ser. No. 561,802, Nov. 22, 1995, abandoned.

[30] Foreign Application Priority Data

Dec. 2, 1994 [IL] Israel ............................................. 11852

[51] Int. Cl.$^6$ ................................................. G05D 25/00
[52] U.S. Cl. ........................................... 250/221; 250/205
[58] Field of Search .................................. 250/221, 205; 372/38, 25

[56] References Cited

U.S. PATENT DOCUMENTS 5,091,627  2/1992  Kimura ............................. 219/121.83
5,229,593  7/1993  Zato .................................... 250/205
5,382,785  1/1995  Rink .................................... 250/205
5,451,765  9/1995  Gerber ................................. 250/205

*Primary Examiner*—Edward P. Westin
*Assistant Examiner*—Kevin Pyo
*Attorney, Agent, or Firm*—Edwin D. Schindler

[57] ABSTRACT

A system for preventing damage to the eyes of a person being within a certain distance from a high-power laser, including a device for ascertaining the absence of a person within this range, and a device for actuating the high power laser only if the results indicate that no such person is present in the specified range. There is also provided a method for eye protection against damage by high-output lasers, which comprises examining such a range with a low power laser or other similar device, harmless to a person's eyes within the specific range, and for actuating high power laser radiation only after a clear indication that no person is present within the dangerous range.

12 Claims, 1 Drawing Sheet

EYE PROTECTION SYSTEM WHEREIN A LOW POWER LASER CONTROLS A HIGH POWER LASER

This is a continuation of application Ser. No. 08/561,802, filed Nov. 22, 1995, now abandoned.

FIELD OF THE INVENTION

The invention relates to laser systems and in particular to a method of rendering eye-safe the use of a laser system which is otherwise non-eyesafe. This is by way of an auxiliary device or modification of existing laser equipment.

BACKGROUND OF THE INVENTION

Lasers and laser-based systems are used extensively in many field applications including rangefinding, remote sensing and others. All of these systems comprise a laser transmitter which emits a relatively high intensity light beam which generally is a potential hazard to the human eye. The eye safety issue in the operation of lasers and laser-based system poses a restriction on the use of such systems.

There exists a growing demand for eye-safe lasers and it proves more difficult to implement this for the industrial and the military fields. In spite of the fact that the military is using a variety of unsafe equipment in the battlefield, in training, the safety issue is most critical, and there is a need to be able to use equipment for battle and for training. In another example, civil engineering type range finding is performed at low energy levels, for eye safety reasons and a retroreflector is used at the target location. The possibility to increase the transmitter energy level without compromising eye safety would improve significantly the equipment performance and its deployment.

To solve problems of using high power lasers without endangering the eye, three approaches exist today:

a) The use of a wavelength of emission where a relatively high intensity radiation can be used without a permanent damage to the retina.
Popular wavelengths are $1.54\mu$ and $10.6\mu$.
This solution is not always optimal, as it reduces system performance and increases cost, and in some applications it is impractical to implement, as there is a cross dependence with external systems which are not wavelength matched. The case of laser designators is an example to such systems.
Moreover, these wavelengths may cause temporary damage to the Cornea or to the Vitreous Humor.

b) The use of temporary attenuators of the laser beam, to a safe radiation level, in potentially hazardous situations.
This method is popular in military training situations and is accompanied by a boost in reflectivity to the training target, to compensate for the lost energy in the transmission.
The attenuation of the laser beam during training is not a true replication of the combat condition as it prevents the opportunity to aim at random targets successfully. It also suffers from a complication of the logistics of attaching special retroreflector to each potential target.

c) A clearly visible marking of the potentially hazardous equipment, to induce the users to take external precautions or avoidance of the laser beam. This minimum mandatory requirement is a very low cost solution to the safety issue but it is operators sensitive and is prone to accidents.

The solutions that are available today to solve the eye safety issue are thus, in many cases only partial solutions to the eye safety issue, are expensive, impractical or reduce significantly system performance.

SUMMARY OF THE INVENTION

It is an object of the present invention to provide a sensing mechanism and a control logic to use with existing laser systems and laser based equipment, which renders the use of these safe to the human eye.

It is a further object of the present invention to provide a sensing mechanism and control logic to new high-power lasers and laser based equipment, which renders these safe to the human eye.

It is a further object of the present invention to provide a substitute for existing laser transmitters for short distance range finding applications.

The sensing mechanism includes a low intensity fight pulse transmitter, possibly a laser diode, whose beam is optically combined or optically aligned with the laser beam of an existing design, or a different mode of operation of the existing laser. The mechanism further comprises optical receiver and processing means, which could be a modification of the existing receiver or an addition to such equipment. Means for remote sensing, or detecting, may include the use of microwaves, millimeter waves, acoustic waves or a laser diode.

The novel mode of operation comprises initiating a low intensity light pulse, that will precede the release of the existing high power laser beam, and establishing the distance of a person in its optical path by calculating the time delay of the returned echo from this person. Such a mode of operation prevents the actuation of the high power laser beam if the measured distance is below the eye-safe distance for such a laser beam. Such operation ensures by using an eye-safe light beam, that there is no object, specifically a human eye in the path of the anticipated laser beam of high eye-damaging intensity.

A system of this invention comprises in addition to the existing laser a comparatively low-power light pulse source that emits its beam through one of the existing optical channels—the transmitting optics through its own optics collimated onto the target of the existing device. The present invention also provides a power supply to drive the light low-power pulse source.

The invention is illustrated with reference to the enclosed FIG. 1, which illustrates a conventional laser combined with an auxiliary system of the invention.

As shown in this FIGURE, the entire system comprises a conventional laser transmitter 11, which is powered by power supply 12 and which is controlled by control logic and processor 13, which laser emits a light beam 14 via beam splitter 15 and via transmitting optics 16 as beam 17 to the object (person).

There is further provided a light pulse power supply 18, connected to control logic and processor 13, which powers light pulse source 19 which emits a light pulse 20 via beam splitter 15 and the same transmitting optics 16 to the object. Light reflected from the object (person) passes via optics 21 to receiver 22 which is connected with the control logic and processor 13. The sensing light pulse from source 19, returned from the object (person) and received by receiver 22 is evaluated by control logic and processor 13, which evaluation is the basis of the decision whether to actuate the Laser Transmitter 11.

Prior to the initiation of the existing laser transmitter 12 by control logic 13 this control logic 13 initiates a triggering signal 13' to the Light pulse power supply 18 which drives the light pulse source 19 to emit a short light pulse 20. This beam, by way of optical combiner 15, will be transmitted through the transmitting optic 16 of the main transmitter 11 and will reach same object the laser system was aimed at. Any object, especially a person, within the path will return a light echo 23, that after going through receiving optics 21, will be detected by the receiver 22. For some applications the receiver 22 will be modified to act at short ranges, down to zero range. The receiver 22 sends a signal to the control logic 13 that uses the delay between the arrival of the echo and the initiation of the light pulse to establish its distance. Unit 13 compares the distance of the object, as deduced from the delay, to the eye-safe distance required by the standard, and will initiate the trigger to operate the laser transmitter 11 only if the distance of the person is greater than the eye-safe distance for the main laser.

In some applications, the use of the above described algorithm will be lacking, as the energy required to sense and measure distance to objects at the minimum eye-safe distance of the existing design, will call for the use of a light pulse source 19, which in itself is not eye-safe at zero distance from the transmitting optics 5.

For such systems the algorithm can be enhanced so that light pulse source can be emitted and processed in a number of consecutive steps. Each step shall be as in the above described algorithm, but the light pulse intensity will be progressively increased with each pulse. The first pulse will be absolutely eye-safe down to zero distance. If the result of the first pulse shows that there is no person in the optical path up to a distance L1 than a stronger second pulse will be emitted to verify that there is no person up to a distance of L2, where L1<L2

The second pulse can be more powerful, as its requirement for eye safety has to be met only down to L1. This can be repeated a number of times with an increasing power from pulse to pulse until full eye-safe conditions are verified.

As an example, using a 10–20 Watts pulsed laser diode as the light pulse source 19, enables to sense objects to 100 meters, is zero range eye-safe and will verify safety for pulsed $1.06\mu$ laser transmitters of about 10 mJ per pulse. Such a 10 mJ transmitter is eye-safe above 100 meters and can serve in rangefinders for 10 km maximum range.

I claim:

1. An eye-safe laser comprising proximity range-measurement sensing means utilizing a low power light source for ascertaining whether a person is present up to the range at which the laser beam will cause eye damage, and means for actuating a high power laser only if no person is present within such a range.

2. A system according to claim 1, which comprises a proximity range-measurement means for actuating the laser at a reduced power output and means for establishing the presence or absence of a person within the range where full laser power will cause eye damage, and depending on the results of this test, means for actuating the full power laser only if no person is within the dangerous range.

3. A system according to claim 1, comprising a subsystem with a low-power output laser, means for using its low power beam for range-measuring to ascertain the presence or absence of a person in the range where eye damage will be caused by the high-power laser, and means for directing said low-power beam in the direction of a target though an optical system for the high-power laser.

4. A system according to claim 3, where the low-power laser beam source is a laser diode.

5. A system according to claim 3, where the low-power output laser is a laser operated at a pulse mode or in a continuous mode.

6. A system according to claim 1, comprising an auxiliary laser of weak power and means to operate it in a mode of operation different from that of the high power laser.

7. A system according to claim 1, comprising means for remote sensing using microwaves, millimeter waves or acoustic waves.

8. A system according to claim 1, incorporated in a range finding or target designating device.

9. A method for protecting a person against damage by laser radiation, which comprises examining a range up to which a high power laser is likely to cause eye damage to the eyes of a person, said examination being effected by proximity range-measurement detecting means utilizing a low power light source selected from a low power laser beam, microwaves, millimeter waves and acoustic waves, and according to the determination that no person is within said range, actuating a high power laser.

10. A method according to claim 9, where a high-power laser is actuated at such reduced power so as not to cause eye damage to a person within a certain range, and after ascertaining that no person is present within said range, actuating said high-power laser at full power.

11. A method according to claim 9, where the low power laser beam is produced by a laser diode.

12. A method according to claim 9, which comprises operating the low-power laser in a pulse mode or in a continuous one, or in a mode of operation different from the mode of operation of the high-power laser.

* * * * *